United States Patent [19]
Risch et al.

[11] Patent Number: 5,177,995
[45] Date of Patent: Jan. 12, 1993

[54] ANALYSIS OF MIGRATION OF A VOLATILE SUBSTANCE DURING HEATING WITH MICROWAVE ENERGY

[75] Inventors: Sara J. Risch, Edina; Kurt Heikkila, Shoreview; Rodney J. Wiliams, Stacy, all of Minn.

[73] Assignee: Golden Valley Microwave Foods, Inc., Edina, Minn.

[21] Appl. No.: 505,714

[22] Filed: Apr. 6, 1990

[51] Int. Cl.⁵ .................................. G01N 30/54
[52] U.S. Cl. ........................................ 73/23.41
[58] Field of Search ............... 73/23.41, 23.35, 23.42, 73/19.02

[56] References Cited

U.S. PATENT DOCUMENTS

4,003,257 1/1977 Fletcher et al. ............... 73/19.02
4,096,734 6/1978 Khayat ........................... 73/23.41
4,617,828 10/1986 Ellebracht ....................... 73/866

Primary Examiner—Hezron E. Williams
Assistant Examiner—Joseph W. Roskos
Attorney, Agent, or Firm—Merchant, Gould, Smith, Edell, Welter & Schmidt

[57] ABSTRACT

A quantitative determination of the identity, origin and migration of a volatile substance or mixture of substances, arising from food or food packaging during heating using microwave energy, can be accomplished. A novel process and equipment are disclosed in which a volatile substance or mixtures of constituent compounds, volatilized into the vapor space within or around microwave cooked food or a microwave cooking container, can be gathered and quantitatively analyzed for the identity, origin, chemical changes, migration routes and final locus of the volatile substance.

15 Claims, 3 Drawing Sheets

ANALYSIS OF MIGRATION OF A VOLATILE SUBSTANCE DURING HEATING WITH MICROWAVE ENERGY

FIELD OF THE INVENTION

The invention relates to a method and apparatus used in the identification and quantitative determination of volatile materials, including the origin, route of migration and final locus, of any volatile substance arising from food or food containers during heating using microwave energy.

Foods and packaging materials can contain a variety of substances that are volatile and also can contain a variety of substances that upon contact with microwave energy, can distill, vaporize, flash, decompose, react, or otherwise generate other volatile substances which can pass into the microwave cooking chamber or into the vapor space held within the cooking container. Such volatile substances can then come to rest in or on the edible substances. As new food substances and packaging materials are developed for sale to the public, a highly sensitive quantitative determination of the identity, origin, chemical changes, migration route and final locus of volatile organic substances is an important part of the development of microwaveable consumable products. This analytical information can be useful in designing food packaging systems, formulating recipes for the manufacture of microwave consumables, and for ensuring that the microwave food products are safe and retain a pleasing appearance, color, odor and flavor. For the purposes of this application, volatile materials means those organic (carbon based) materials whose vapor pressure at cooking temperatures are such that a substantial proportion of the material, i.e., more than 0.5 wt-%, become a gas, a vapor or a suspension of finely divided particles (an aerosol or mist) dispersed into the cooking environment. A volatile material in the context of this invention can have a molecular weight of less than about 500, and can exist initially in a solid or liquid state in a food substance or a packaging material before heating and can also exist in the form of a vapor, gas or dispersed substance after heating. Synonyms for volatile substance as used herein can include gas, volatile, gaseous monomer, gaseous oligomer, gaseous solvent, aerosol, steam distillate, and others.

For the purposes of this application, "organic substance" indicates one or more organic compounds present in food or food packaging which can be volatilized during microwave cooking. The term "entrains" or "entrain" indicates that as a mobile phase passes through a container, any volatile material and water vapor or steam present become uniformly mixed with the gas phase and are carried along with the gas phase. By the term "constituent compounds" we mean that the volatile organic substance can contain a variety of separable distinct organic compounds which can be identified using a separation device such as a gas or a liquid chromatograph, and identifying instrumentation such as NMR, IR, mass spectrometry, or other instrumentation.

BACKGROUND OF THE INVENTION

Microwave cooking is based on the absorption of microwave energy by polar substances in food and food packaging. The absorbed microwave energy can be re-emitted by polar substances within the food components in the form of heat energy. The water content of food is primarily responsible for absorbing microwave energy and re-emitting the energy as heat. Additionally, foods can be heated by contacting microwave energy with susceptor surfaces or heating devices within microwave cooking containers which absorb microwave energy and then transfer absorbed energy into the food as heat. Such heating modes can result in the creation of locally high temperatures in certain hotspots in foods, on portions of susceptor surfaces or in other heated surfaces that range from 90° F. to 500° F. and in some cases even higher.

A large variety of foods and food container materials are currently being used in microwave cooking. Both solid, semi-solid and liquid food substances, available for breakfast, brunch, lunch, dinner or snack time consumption have been adapted for microwave cooking. In order to provide the foods in a pleasing, easily-used package, a variety of materials have found a use in microwave cooking including a variety of inorganic materials, organic films and fibers. Additionally, structural thermoplastic and thermosetting materials can be used. Further, ceramics, paper, cardboard, metallized polyester, etc., are used. Susceptor materials, used as sources of heat for certain applications, most commonly comprise a film or sheet, such as Mylar, a polyethylene teraphthalate polyester, with finely divided aluminum particles imbedded in or deposited on, the film or sheet material. Such sheets are placed in the microwave cooking container directly adjacent to the food substance to introduce heat directly into the food.

Because of the variety of food substances and the variety of packaging materials used in cooking containers, a variety of volatile substances with large amounts of steam or water vapor can be introduced into the vapor space of the microwave oven or the vapor space within the cooking container. Such materials are created or driven from the food or container materials by the action of heat on the volatile material and other substances in the food. Examples of volatile substances that could arise during cooking include water, thermal decomposition products of food materials and packaging materials, volatile substances that are volatilized or steam distilled from the packaging or food substances and new reactive species created by reaction, in the vapor space, of reactive volatile materials driven from the food or package material.

The production of such volatile materials during microwave heating of food and packaging materials has created significant interest and concern in the identification and quantitative determination of the amounts of materials produced. Further, a great deal of interest has been focused on identifying the origin, the production mode, the transportation mode from the food or other material through the vapor space of the packaging material and oven interior, and final point of migration of volatile substances. The volatilization and migration of such volatile substances can change the color, flavor and texture of foods, can change the nature or integrity of packaging materials, and in certain cases could potentially result in the concentration of undesirable or even toxic substances in foods or packaging materials after heating.

Such a need has been present during the years microwave ovens have been available. A technique known as microwave head space analysis a packaging material has been used by NFPA/SPI. This method involves placing 1 to 5 grams of materials to be analyzed within a small head space container in a microwave oven adjacent to a large volume (100–500 ml) of water. The microwave oven is operated and decomposition or volatilization of compounds occurs within the head space vial. The head space vial is then transferred to a head space analyzer which injects the material into a gas chromatograph analyzer wherein the materials are transferred to the analytical column and analyzed. We have found that for the purposes of the precise determination of origin, identity, chemical changes, migration and final locus measurements that this head space analytical procedure is insufficient in producing reliable data for many food and packaging systems. However, even view of the fact that a variety of analytical techniques for the identification and quantitization of variety of chemical substances have been known, the prior art has never disclosed a quick, simple method and apparatus for directly determining the identity of volatile substances, or for quantifying the amount of such substances and tracing the production mode and final locus of volatile material in either food packaging or microwave oven after cooking.

Accordingly, a substantial need exists for an analytical technique that permits identifying the chemical nature of and amount of a volatile substance optionally in the presence of large amounts of steam or water vapor produced during microwave heating derived from foods and microwave packaging and cooking materials. Further, a need exists for the determination of the locus of origin of such volatile substance, any chemical change in the substance, the mode of production, transport and the final locus of such a substance that can migrate during cooking.

BRIEF DESCRIPTION OF THE INVENTION

We have found that in microwave heating of foods and packaging substrates, that volatile substances are created and can be generated in conjunction with large volumes of vaporized or volatilized water. When present, the weight ratio of volatile water to volatile substances produced and migrating to food substances is on the order of $10^6$ to 0.1 or more commonly, $10^5$ to 10 parts of water per part of volatile substance. Because of large quantities of water, a method is required that can trap all the volatile material in the presence of large quantities of volatilized water.

We have found an analytical system comprising a generator vessel, a trap and a sample/purge system that can be used to produce and collect volatile substances from microwave heated foods. The volatile substance can then be applied from the sample purge system to a GC (gas chromatograph), MS (mass spectrometer) or both for identification and quantitization.

The generator comprises a substantially microwave transparent vessel, used to enclose, during microwave heating, the microwave food, the packaging or both, having an inlet for an inert mobile gas phase and an outlet for the gas phase, which can entrain and carry the volatile substance from the vessel. The inlet directs the inert gas into the generator vessel wherein the gas phase removes volatile materials leaving the food or packaging into the vapor phase. The outlet directs the mobile gas phase through a gas conduit into a low temperature or cryogenic trap operated at a sufficiently low temperature such that essentially all water and volatile materials are held in the trap in solid form.

A sample/purge unit is used wherein the entire contents of the volatile materials in cryogenic trap can be quantitatively sampled and adsorbed while the majority of the water remains in the trap. The volatile substances are then purged and introduced into a gas chromatograph for separation and further identification by mass spectrometry. The components of the invention have the unique ability to (1) generate and mobilize the volatile substance from food or packaging, (2) quantitatively trap and retain water and the materials released from the cooked foods and packaging materials, (3) maintain the volatile materials in a useful unmodified form, (4) separate the volatile materials from the majority of water and (5) introduce the volatile material into the liquid or gas chromatograph or other separation/analytical equipment at a convenient time for analysis.

To the best of our knowledge, to date, with a significant need for this capability, the microwave foods industry has been unable to monitor or quantify volatile substances arising from either food or packaging, to identify their origin, transportation mode or final locus of such substances when cooking is complete.

DETAILED DISCUSSION OF THE INVENTION

Figure 2:
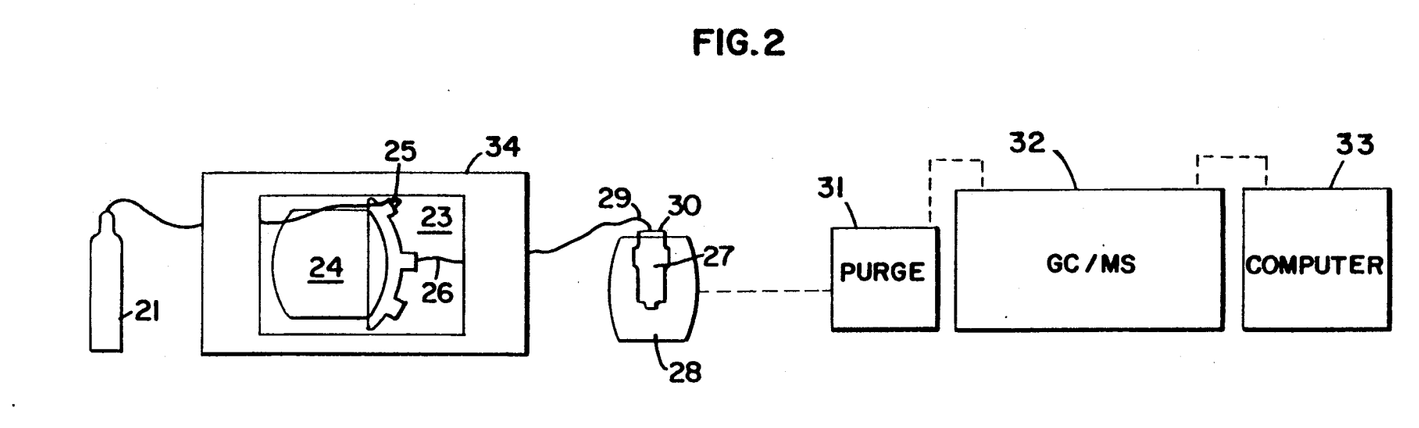
FIG. 2 is a schematic representation of the analytical apparatus of the invention that generates, traps and analyzes volatile substances.

The analytical method of the invention which can identify, quantify and determine the site of origin, migration and final locus of volatile substances produced during microwave cooking involves first, generating the volatile substance by heating the food, the packaging material or both in a generator vessel held within a microwave oven. FIG. 2 is a representation of equipment that can be used to perform such an analysis. The generator vessel 24 is equipped with a source of gas or mobile phase 21, a gas inlet 25 and a gas outlet 26 for the purpose of delivering a mobile gas phase through the generator vessel which entrains the volatile substances, removes the volatile substances from the generator vessel 24 and directs the materials into a low temperature trap 27 in a cooled reservoir 28. The mobile phase enters an inlet 29 and after removal of the water and volatile substance leaves outlet 30.

Figure 1:
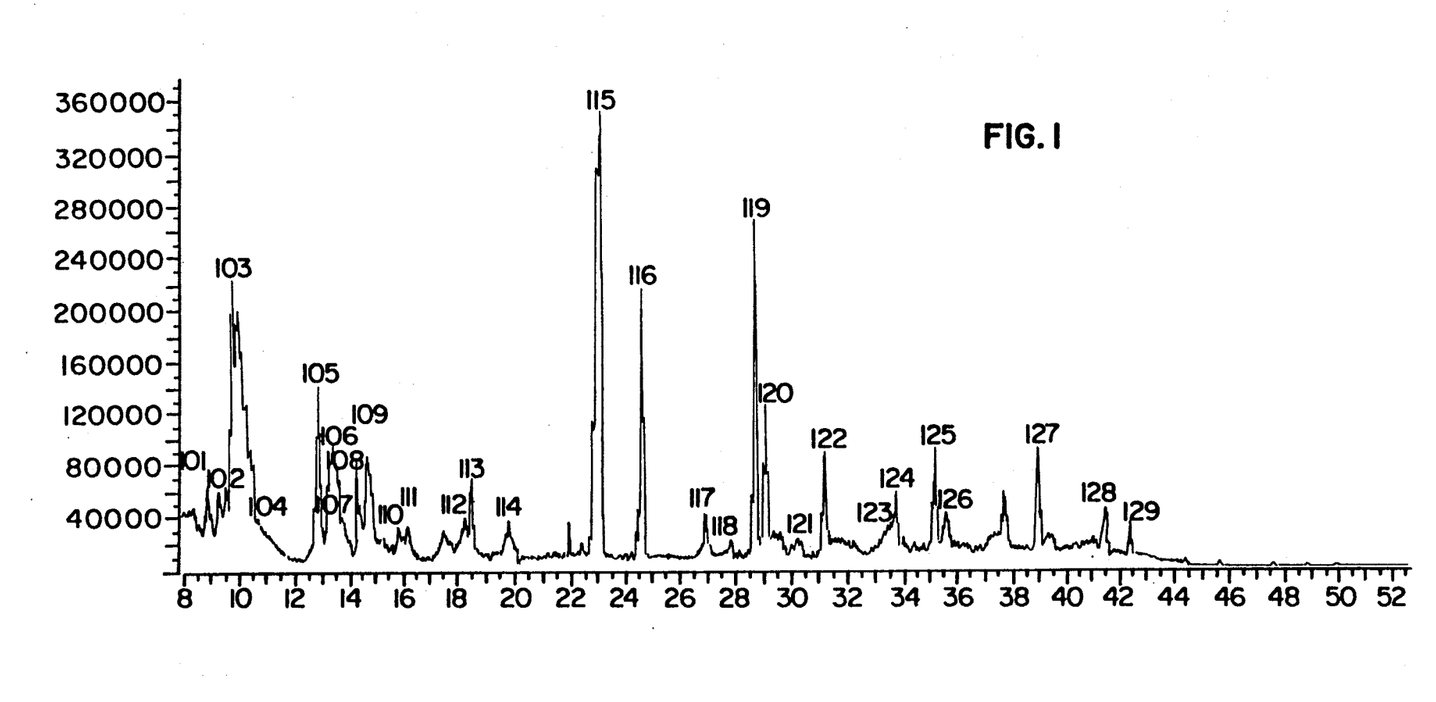
FIG. 1 represents a typical total ion chromatogram showing constituent compounds of volatile substance derived from analysis of snack foods prepared in a microwave oven.

The low temperature in the cryogenic trap 27 causes the volatile substance and any water generated during heating to be trapped as a solid. The volatile substance is separated from the water in a purge unit 31 and analyzed in a gas chromatograph/mass spectrometer 32. FIG. 1 shows a typical total ion spectrum of separated constituent compounds in a volatile substance. Data can be accumulated and analyzed in a dedicated computer 33.

Figure 3:
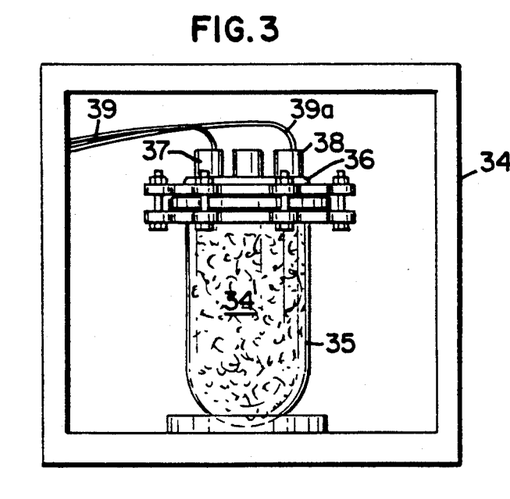
FIG. 3 represents a generator (reactor) vessel within a microwave oven cooking chamber, having an input for the mobile phase and an output directing the gas phase to the low temperature trap.

The generator vessel 24 can be fabricated from any microwave transparent material that can be configured with a gas inlet and a gas outlet for the mobile gas phase. Commonly, as shown in FIG. 3, the generator vessel 24 can be installed in a microwave oven 34, comprises a container portion 35 and a cover portion 36. Either the container 35, the cover 36, or both can be configured with the gas inlet 37 or the gas outlet 38. The generator vessel 34 can be made from glass, ceramics, thermoplastic materials, thermosetting structural materials, or other relatively inert materials common in the fabrication of containers or vessels. The container 35 is preferably made of visually transparent material to permit the operators to visualize the cooking cycle and to observe changes in production of volatile substance, changes in the appearance of the food, and to observe passage of the mobile phase through the food substance. Such transparent materials include glass, high impact polystyrene, acrylic polymers, polycarbonate materials, etc. The preferred generator material is chemically inert to water and typical volatile substances produced in the cooking of food materials; and is resistent to the absorption of water or the volatile substances. If necessary, the interior of the generator can be lined with a glass or other removable insert to protect the generator material from undesirable interactions with the volatilized water or volatile substances.

Preferably, the generator vessel is equipped with inlet 37 and outlet 38 for attaching an inlet 39 conduit or an outlet conduit 39a for the introduction of a mobile gas phase into the generator and conducting the gas phase plus any entrained material from the generator to a cryogenic trap. Such materials are similar to that used in the fabrication of the generator vessel 24 and trap 27.

The mobile gas phase used in entraining volatile substances during cooking of the foods or heating of packaging material can be any gas compatible with the volatile substance. By compatibility we mean that no significant modifications to the volatile substances occur during heating in the presence of the gas phase. For these reasons, nitrogen, argon, filtered-dry air, and carbon dioxide are preferred mobile gas phases. Nitrogen being the most preferred gas for reasons of economy and utility in the method of the invention.

Conduits 39, 39a that can be used to carry the gas phase from its source to the generator vessel and carry the gas phase with the entrained volatile materials to the cryogenic trap are typically flexible conduits made from stable microwavable substances including such thermoplastics as polyethylene, polypropylene, nylon, polycarbonate, polystyrene, glass, etc. The primary function of the conduits is to be a carrier of the mobile phase from place to place and as such needs only to withstand and maintain moderate pressure and temperatures.

Figure 4:
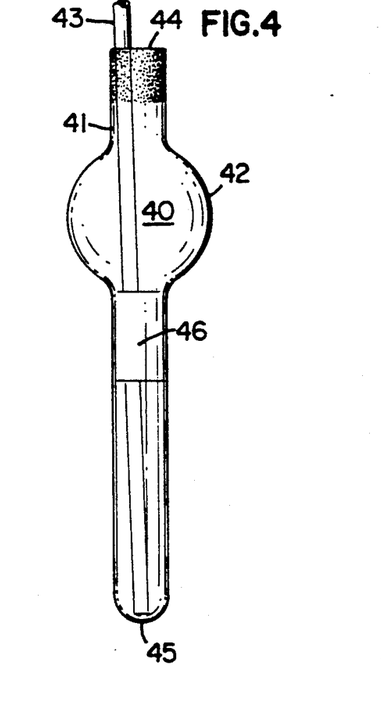
FIG. 4 represents a low temperature trap.

After the volatile substances are produced by microwave heating of the food substance or the packaged material, the mobile gas phase transfers the volatile materials from the generator vessel into a low temperature trap 40 shown in FIG. 4 (trap 27, FIG. 2). The trap 40 ensures that all volatile substance and water generated during microwave heating are condensed and held in the low temperature trap in solid form. In the preferred mode, the low temperature trap 40 comprises a cylindrical container 41 having an expanded portion 42, inlet 43 for the mobile gas phase, and an outlet 44 for the gas phase after the volatile substances in the water have been removed. Preferably, the inlet 43, for the mobile phase and volatile substances is directed to the bottom 45 of the low temperature trap forcing the mobile phase to be introduced at the bottom of the trap 45 and also forcing the mobile phase to rise from the bottom of the trap to the outlet portion 43. As the mobile phase rises in the trap 40, the low temperature of surfaces in the trap 40 causes the volatile substances to freeze. The immobilization of the materials within the trap 40 can be significantly enhanced by introducing a packing material 46 within the trap 40 which provides additional low temperature surfaces for condensation and trapping of volatile substances. The trap 40 should be of sufficient length to ensure that the volatile material is fully solidified before the carrier gas removes the material from the packaging and trap 40. The trap 40 should also be configured such that it can be easily inserted into a cold reservoir of acetone/dry ice or liquid nitrogen. Further, the trap 40 can be easily moved and detached through the separation/analytical devices for identification of volatile substances.

The trap packing or trapping material 46 can preferably be material having large surface area providing opportunity for the volatile materials to freeze or solidify. A variety of packing materials are commonly available and used in such traps including glass helicies, glass saddles, glass woven mesh, glass beads, boiling chips, glass wool or fleece, finely divided silica, teflon chips, etc. Such packing material should be inert to the volatile substances, be finely divided, should not cause significant pressure drop and should be easily introduced into the trap.

The trap itself is made of an inert material including materials listed above for use in the generator vessel. Preferably, the trap is made from glass.

The mobile gas phase can be introduced into the generator/trap mechanism of the invention at or above ambient pressure and at a flow rate of about 0.1 to 5, preferably 0.2 to 2 liters per minute. The pressure must be sufficient to move the gas phase through the apparatus but not so great as to cause the failure of the conduit, generator or trap. The flow rate should be sufficient to cause the volatile substances to be entrained and removed from the generator and transferred into the trap but not be at such a high flow rate that the trap cannot solidify the entire amount of volatile substances produced. The gas phase can be preheated at the source, in any of the conduits between the source, the generator, the generator and the trap. Such preheating can increase the efficiency of entraining the volatile substances without undesired condensation of water or other bottled substances in the conduits ensuring that the entire production of volatile substances is transferred into the trap.

After the trap 40 has accumulated and solidified all volatiles substances in water from the food or the package, the trap 40 is removed to a sample/purge unit a convey the entire contents of volatile substance to the analytical device. The portion of the trap containing the solidified frozen water and volatile substances is placed into the heating device capable of raising the temperature of the trapped portion to a temperature less than the boiling point of the water. Preferably to maintain adequate control over the recovery of the volatile substances with mineral water the temperature of the trap is maintained at less than about 98° C. or lower depending on ambient pressure, preferably 85° to 95° C., which causes the majority of the water to remain in the trap while causing the volatile substances to be conveyed from the trap into the analytical device. The gas stream from the heated trap can be conveyed directly to the column in the gas chromatograph. However, preferably the stream from the heated trap is driven to a secondary column within the analytical device which contains absorbent material which recovers essentially all the volatile materials from the gas stream leaving the heated trap.

Figure 5:
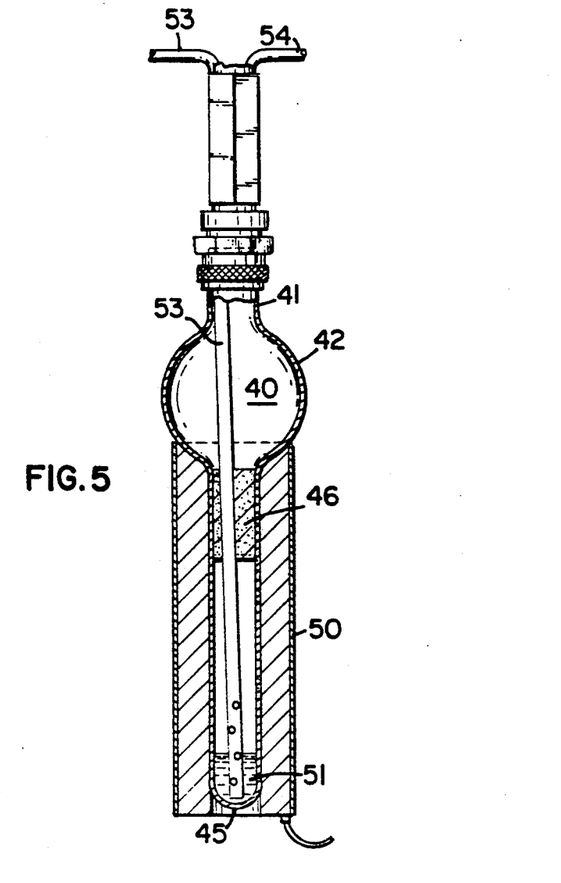
FIG. 5 represents a low temperature trap in a configuration that can release the volatile materials to the analytical device.

FIG. 5 represents the cryogenic trap 40 that has been removed from the low temperature reservoir and inserted into an annular heating device 50. The annular heating device 50 is electrically heated to a temperature less than the boiling point of water and preferably between 80° and 95° C. The water and volatile substances 51 melt and collect in the bottom of the trap 40. A portion of the volatile substances can be present in the packing 46. A second mobile phase is introduced through the conduit 53 into the liquid water and volatile substance 51. The second mobil phase entrains the volatile substance in the mobile phase leaving the majority of the water in the cryogenic trap. The mobile phase leaves the cryogenic trap at the attachment point 54 of the trap to the sample purge unit. Within the sample purge unit, the mobile phase is directed to an absorbent containing blended materials uniquely adapted to ensure complete absorption of all volatile substances driven from the cryogenic trap by the heater 50. After all the volatile substance has been recovered from the cryogenic trap and transferred to the absorbent on the absorbent material, the absorbent material is then heated to again volatilize the materials which is then directed into the gas chromatograph mass spectrograph.

We have measured recovery of volatile substances from the heated trap by means of adding deuterated benzene or other internal control materials either to the food, or the trapped solids and measuring the efficiency of recovery of the materials. We have found that we reproducibly recover internally added standard materials.

The analytical method of the invention can be used to analyze the substances arising directly from the food substance by heating the food substance in the absence of packaging materials and determining the volatile materials released by the food during cooking. The packaging materials can be heated in the absence of any food materials to identify and quantify the volatile material derived from the packaging. Further, any component of the food or packaging material such as recipe ingredient, food coloring, preservative or other additive can be singly heated and tested for generation of volatile substances. The individual packaging materials such as printing inks, paper, susceptor materials, polyester sheets, finely divided aluminum particles or any other component used in the production of the packaging materials can be separately heated and tested for production of volatile materials. Using these analytical devices, the origin of any volatile substance produced in microwave heating of food or packaging materials can be traced to its origin. Further, using the analytical device and methods of this invention, the final locus of any volatile substance can be measured by heating the food and packaging material in the oven and after the foods have cooled, heating the food to measure the concentration of volatile substances present in the material. With the knowledge of the origin and final locus of the food materials, the migration roots of the volatile substance can easily be traced. Further, any decomposition or chemical change in any of the volatile substances can be monitored by fractionating the volatile substances produced during cooking and watching for any reaction in which once substance is converted (its concentration will drop with time) into another substance whose concentration will increase with time. The resulting information is a powerful analytical tool to aid in control of product quality in the manufacture of microwaveable food substances.

WORKING EXAMPLES

Into a 1,000 ml KIMAX reaction vessel equipped with a lid attached using a screw clamp was placed a commercial microwave popcorn product containing corn and oil held within a paper bag having a MYLAR aluminum susceptor layer. Through the KIMAX vessel was passed a stream of nitrogen at about meliter per minute at near ambient pressure. The nitrogen stream was directed to a cryogenic trap in a liquid nitrogen bath held at −178° F. The KIMAX vessel was installed in a commercial 750 watt microwave oven and was cooked for approximately 4 minutes. During cooking, the nitrogen stream entrailed volatile materials released by the cooking of the popcorn oil and bag and transferred the materials into the cryogenic trap where they were frozen and retained. The trap tube with frozen material was placed in an annular heater and was heated to 90° C. A nitrogen stream at one liter per minute transferred the volatile material to an adsorption in a sample/purge unit. The collected material was desorbed into a GC/MS system. This general procedure was repeated to produce the data shown below with the individual components of the commercial popcorn product and with additionally intentionally added internal standards as described.

INITIAL TESTING

Initial testing was conducted using microwave heated popcorn snack food as a prototype food/package system. The initial results showed there was no transfer of any components of the package into the popcorn. Empty packages were heated to identify the compounds which were generated during microwave heating. The concentration of compounds generated was in the parts per billion range. Popcorn that had been cooked in the package was analyzed specifically for the compounds evolved by the package. None of the compounds were found in the popcorn.

The overall objective of this study was to determine the identity, concentration, source, and retention of volatile organic compounds which are emitted during microwave heating of the popcorn.

A list of volatile compounds (see Table I) that we have detected and could be produced by our packaging was determined from preliminary testing. FIG. 1 shows a typical total ion spectrum. The compounds from this list which are of greatest potential toxicological concern or present in the largest concentrations were purchased as analytical standards to determine a detection limit as well as for use as confirmatory analytical standards. These compounds are designated (in Table I) with asterisks. The concentration of each of these in terms of ug/in$^2$ of packaging material (shown in Table II). We followed an EPA protocol for the process of analyzing each compound by GC/MS examination of the ions that are produced, and the levels for each of the ions by mass spectrometry. This method is used for both compound identification and quantification.

TABLE I

| Peak # | Case # | Compound |
|---|---|---|
| 101 | 75650 | 2-methyl-2-Propanol |

TABLE I-continued

| Peak # | Case # | Compound |
|---|---|---|
| 102 | 123397 | N-methyl-Formamide |
| 103 | 534225 | 2-methyl-Furan |
| 104 | 78933 | 2-Butanone |
| 105* | 71432 | Benzene |
| 106 | 78853 | 2-methyl-2-Propanol |
| 107 | 4170303 | 2-Butenal |
| 108 | 543759 | 2,3-dihydro-1,4-Dioxane |
| 109 | 600146 | 2,3-Pentanedione |
| 110 | 108952 | Phenol |
| 111 | 123911 | 1,4-Dioxane |
| 112 | 930303 | 2-Cyclopenten-1-one |
| 113 | 930278 | 3-methyl-Furan |
| 114 | 115117 | 2-methyl-1-Propene |
| 115* | 98011 | 2-Furancarboxaldehyde |
| 116 | 694871 | Bicyclo[4.2.0]octa-1,3,5-triene |
| 117 | 611154 | 1-ethenyl-2-methyl-Benzene |
| 118 | 17302282 | 2,6-dimethyl-Nonane |
| 119* | 98839 | (1-methylethenyl)-Benzene |
| 120* | 100527 | Benzaldehyde |
| 121 | 1587048 | 1-methyl-2-(2-propenyl)-Benzene |
| 122 | 1120214 | Undecane |
| 123 | 6044719 | 6-methyl-Dodecane |
| 124 | 579077 | 1-phenyl-1,2-Propanedione |
| 125* | 112403 | Dodecane |
| 126 | 6044719 | 6-methyl-Dodecane |
| 127* | 629505 | Tridecane |
| 128 | 17302328 | 2,7,10-trimethyl-Dodecane |
| 129 | 629594 | Tetradecane |

TABLE II

| * | Compound | Concentration (mg/in$^2$) |
|---|---|---|
| 105 | Benzene | 0.0044 |
| 115 | 2-Furancarboxaldehyde | 41.5100 |
| 119 | Styrene | 0.0440 |
| 120 | Benzaldehyde | 0.3800 |
| 125 | Dodecane | 0.0540 |
| 127 | Tridecane | 0.1000 |

The cyro-trap which is outside the oven consists of a vessel packed with glass wool. The glass wool facilitates trapping of the compounds which are present in an excess of steam. Once the purging of the generator is complete, the trap is transferred to a purge and trap system (O.I. Corporation) attached to a GC/MS.

By doing a series of recovery experiments with target materials identified int he previous set of experiments, an analytical method was created to isolate volatiles of the cooking process and the volatiles evolved from the packaging and the food. These materials were then trapped outside of the microwave oven and were subsequently thermally desorbed into a gas chromatograph-/mass spectrometer to be submitted to the same type of compound analysis and the same type of compound analysis and quantitation scheme as in the first part of this project. A block diagram of the analytical equipment is shown in FIG. 2. This cooking process allowed us to reproduce the work and quantify the amount of materials that come off the packaging, and that come off the food, during the microwave cooking process.

The data presented in Table III shows that the packaging, the oil and the popcorn each has its own volatile constituents that are evolved during the microwave cooking process. This serial experiment allowed us to determine which volatiles come from which source (packaging, oil, and popcorn) during the microwave cooking process as well as to validate the analytical recovery.

TABLE III

Volatile Constituents Evolved from Oil, Oil and Corn, and Complete Package

| Analyte STD | Package & Oil & Corn | Package & Oil & Corn | Oil | Oil & Corn |
|---|---|---|---|---|
| Bromochloromethane* 0.16 | 0.16 | 0.16 | 0.16 | 0.16 |
| 1,4-Difluorobenzene* 0.16 | 0.16 | 0.16 | 0.16 | 0.16 |
| Benzene 0.18 | 0.0087 | 0.0028 | 0.00032 | nd |
| Toluene 0.16 | 0.025 | 0.013 | 0.013 | 0.011 |
| Chlorobenzene-d$_5$* 0.16 | 0.16 | 0.16 | 0.16 | 0.16 |
| n-butyl Ether 0.11 | 0.028 | 0.0095 | 0.00061 | nd |
| 2-Furancarboxaldehyde 30.08 | 22.65 | 9.80 | nd | 26.33 |
| Styrene 0.20 | 0.011 | 0.0044 | nd | 0.00070 |
| Benzaldehyde 4.76 | nd | nd | nd | nd |
| 2-ethyl-1-Hexanol 1.61 | 0.73 | 0.17 | nd | 0.00026 |
| Dodecane 1.61 | 0.40 | 0.13 | 0.0020 | 0.0076 |

*denotes std
All concentrations in ug/in$^2$

These data also allowed us to look at the mechanism for volatiles being evolved in the microwave cooking application. By using the same target compounds and spiking them into a reactor and into known amounts of oil and popcorn (Table IV) we validated the recoveries that we obtained in our first experiments. These data are augmented by the use of internal standard compounds which validate the analytical recovery of the microwave cooking application. This quantification of using spiking materials, surrogate materials, and internal standards to compensate analytical methods for matrix effects are well recognized by EPA methodology.

TABLE IV

Recoveries of Target Compounds from Oil and Corn and Complete Product as a Percentage of the Spiked Amount of that Compound

| Spike Package & Analyte Corn | Oil & Corn | Oil & Corn | Spike Package & Oil & Corn | Oil & |
|---|---|---|---|---|
| Bromochloromethane* na | na | na | na | |
| 1,4-Difluorobenzene* na | na | na | na | |
| Benzene 92% | 56% | 40% | 150% | |
| Toluene 140% | 81% | 55% | 310% | |
| Chlorobenzene-d$_5$* na | na | na | na | |
| n-butyl Ether 310% | 100% | 58% | 370% | |
| 2-Furancarboxaldehyde 210% | 140% | 150% | 110% | |
| Styrene 110% | 62% | 40% | 130% | |
| Benzaldehyde nd | 55% | 46% | nd | |
| 2-ethyl-1-Hexanol | nd | nd | 2900% | |

TABLE IV-continued

Recoveries of Target Compounds from Oil
and Corn and Complete Product as a
Percentage of the Spiked Amount of that Compound

| Spike Package & Analyte Corn | Oil & Corn | Oil & Corn | Spike Package & Oil & Corn | Oil & |
|---|---|---|---|---|
| 2400% Dodecane 86% | 43% | 31% | 53% | |

*denotes lstd
na = not applicable
nd = not detected

The conclusions of the experiments are as follows. (1) There are volatiles which are produced during microwave cooking by popcorn, oil, and packaging. (2) We get good quantitative recovery of the materials in our trapping system, which indicates that a steam distillation process also is occurring. This is recognized by the fact that a large amount of water is also collected during analysis of the volatiles. Based on the reactor, by doing a mass balance type of quantification for this cooking process, we can determine that the cooking process distills out the water as well as the volatiles. The volume of steam is equivalent to 6.5 to 7 times the volume of the expanded bag.

One compound of interest that is a degradation product formed when paper is heated is 2-furfural. The amount of 2-furfural produced by the package is directly proportional to the temperature attained during heating. The bag has been seen to produce anywhere from 1 to 10 mg/in$^2$. Popcorn and oil popped alone without the susceptor present produces 5 to 10 parts per million (ppm) based on the weight of the corn and oil. This is equivalent to 25 to 50 mg/in$^2$. Based on this, the corn is producing 2.5 to 50 times as much furfural as the package.

The final part of the volatiles study confirmed that none of the volatile compounds produced by microwave cooking of the packaging and food can be found in the popcorn. While the mass balance data showed that the compounds generated by the packaging during microwave cooking could be completely recovered outside of the oven, it was still important to look at the food itself. The initial target compound chosen for analysis and validation was benzene. A summary of the recovery and detection limit for benzene in microwave popcorn is provided in Table V. At this point, replicate samples have been run for benzene and work is continuing to have several compounds documented at a statistically significant level.

TABLE V

Determination of Benzene and Benzene-d6

| Benzene-d6 Recovery Run # | Benzene ug/Kg | Benzene ug/sq. in. | Benzene-d6 ug/Kg | % |
|---|---|---|---|---|
| Spiked Popcorn 1 | ND | ND | 6.0 | 40 |
| Spiked Popcorn 2 | ND | ND | 6.1 | 40 |
| Spiked Popcorn 3 | ND | ND | 6.1 | 41 |
| Spiked Popcorn 4 | ND | ND | 5.1 | 38 |
| Spiked Popcorn 5 | ND | ND | 5.3 | 35 |
| Spiked Popcorn 6 | ND | ND | 7.7 | 51 |
| Spiked Popcorn 7 | ND | ND | 5.6 | 36 |
| Spiked Blank 1 | ND | ND | 7.7 | 52 |
| Spiked Blank 2 | ND | ND | 7.9 | 53 |
| MDL | 0.24 | 0.0012 | | |
| | | | Average Benzene-d6 | Std. Deviation of Benzene-d6 |

TABLE V-continued.

| | % | % |
|---|---|---|
| Spiked Popcorn-7 Runs | 40 | 5.3 |

For this work, a deuterated compound, D$_6$ benzene, was chosen to prove system recovery as a surrogate standard. A series of experiments showed that the GC column being used could separated the deuterated from non-deuterated compound and could also be distinguished by mass spectrometry. The same reactor cell that was used in the mass balance study was used for this work. The reactor cell wa placed in a heat jacket with the temperature controlled at 105° C. A known amount of D$_6$ benzene, 11 ug, was added to the empty reactor. The reactor was purged for 5 minutes and 1 L/min nitrogen into a trap packed with glass wool. After purging, the trap was transferred to the purge and trap on the GC/MS. The response for this reactor recovery for D$_6$ benzene was 40% for the system (see Table V).

The next step was to pop popcorn in a package in the microwave oven. Following popping, the corn was transferred to the reactor cell and 1 ug of D$_6$ benzene was added to the cell. The cell was purged and the trap transferred to the GC/MS as previously described. The recovery of the D$_6$ benzene was the same as for the empty reactor. No benzene was detected in the popcorn with a detection limit of 0.0012 ug/in$^2$ which can be achieved with our cryotrapping procedures. This is a factor of 50 less than what is considered an insignificant risk based on existing toxicological data for benzene and consumption factors for microwave popcorn.

The above specification, tables of data and drawings provide a detailed explanation of the apparatus and method of the invention generally and as applied to the analysis of popcorn, microwaveable popcorn containers and to the volatile substances derived therefrom. Since a variety of embodiments of the invention can be made without departing from the spirit and scope of the invention, the invention resides in the claims hereinafter appended.

I claim:

1. A method of isolating and analyzing an organic substance volatilized with large amounts of water, during the microwave induced heating of a food or a food package, which method comprises:
    (a) heating the food or the food package in a sealed vessel having an inlet and an outlet for a mobile phase, while passing the mobile phase through the vessel, which mobile phase entrains the organic substance and the water;
    (b) contacting the mobile phase, and the entrained organic substance and water, with a cold trap at a sufficiently low temperature to quantitatively trap the organic substance;
    (c) heating the trap, the organic substance and water to a temperature below the boiling point of water while passing a second mobile phase through the trap, which second phase entrains the organic substance but leaves a majority of the water in the trap;
    (d) contacting the second mobile phase and the entrained organic substance with an absorbent material, quantitatively transferring the organic substance from the trap to the absorbent material; and (e) desorbing the organic material from the absorbent material into an analytical device that can separate the organic material into its constituent compounds.

2. The method of claim 1 wherein the mobile gas phase comprises nitrogen.

3. The method of claim 1 wherein the cold trap contains a packing and is maintained at a temperature below −80° C.

4. The method of claim 1 wherein the cold trap is heated in step (1)(c) to a temperature between 80°–95° C.

5. The method of claim 1 wherein the absorbent material is held within a column and the second mobile gas phase is passed through the column.

6. The method of claim 1 wherein the analytical device comprises a gas chromatograph-mass spectrometry system.

7. A device for the generation and isolation of water and a volatile substance, from a food or from a food package, generated through the action of microwave heating, which device comprises:
- (a) a source of a mobile gas phase;
- (b) a vessel, having an inlet, in gas communication with the source of the mobile gas phase, and an outlet for the mobile gas phase; and
- (c) a cryogenic trap, maintained at a temperature sufficiently low to quantitatively trap the volatile material, having an inlet in gas communication with the outlet of the generator vessel, having sufficient surface area to substantially quantitatively trap the volatile substance and water.

8. The device of claim 7 wherein the mobile gas phase comprises nitrogen gas.

9. The device of claim 7 wherein the vessel has an internal volume of about 500 to 5,000 ml.

10. The device of claim 7 wherein the vessel is equipped with a source of 750 watts of microwave energy.

11. The device of claim 7 wherein the cryogenic trap is maintained at a temperature of less than −80° C.

12. The device of claim 7 wherein the cryogenic trap is maintained at a temperature of less than −160° C.

13. The device of claim 7 wherein a portion of the surface area of the cryogenic trap is provided through a packing.

14. The device of claim 7 wherein the packing comprises glass wool.

15. A method of isolating and analyzing an organic substance volatilized with water, during heating of a food and/or a food package; said method comprising the steps of:
- (a) heating the food and/or food package in a sealed vessel having an inlet and outlet for a mobile phase, while passing a mobile phase through the sealed vessel;
- (b) entraining the organic substance and water in the mobile phase;
- (c) directing the mobile phase through a cold trap at a sufficiently low temperature to remove the organic substance from the mobile phase and also trap water;
- (d) heating the trap and the organic substance to a temperature below the boiling point of water, while passing a second mobile phase through the trap, and entraining the organic substance in the second mobile phase while leaving a major portion of the trapped water in the trap;
- (e) removing the entrained organic material from the second mobile phase by absorption; and,
- (f) directing the organic material, which has been removed from the second mobile phase by absorption, into an analytical device for analysis.

* * * * *

UNITED STATES PATENT AND TRADEMARK OFFICE
CERTIFICATE OF CORRECTION

PATENT NO. : 5,177,995

DATED : January 12, 1993

INVENTOR(S) : Sara J. Risch; Kurt Heikkila; Rodney J. Williams

It is certified that error appears in the above-identified patent and that said Letters Patent is hereby corrected as shown below:

Column 4, line 68, after the numeral "24", insert --, which--.

Column 6, line 51, delete "volatiles" and insert therefor --volatile--.

Column 6, line 52, delete "a" and insert therefor --to--. (second occurrence).

Column 7, line 15, delete "mobil" and insert therefor --mobile--.

Column 7, line 19, delete "sample purge" and insert therefor --sample/purge--.

Column 7, lines 19 and 20, delete "sample purge" and insert therefor --sample/purge--.

Column 9, line 39, delete "cyro" and insert therefor --cryo--.

Column 9, line 46, delete "int he" and insert therefor --in the--.

Column 10, line 50, under the word "Analyte", delete --Corn--.

Column 10, line 50, after the words "Oil &", insert --Corn--.

Column 11, line 8, under the word "Analyte", delete --Corn--.

Column 11, line 8, after the words "Oil &", insert --Corn--.

Column 12, line 9, delete "separated" and insert therefor --separate--.

Column 12, line 13, delete "wa" and insert therefor --was--.

Column 12, line 17, delete "nitrogen into" and insert therefor --nitrogen directed into--.

UNITED STATES PATENT AND TRADEMARK OFFICE
CERTIFICATE OF CORRECTION

PATENT NO. : 5,177,995
DATED : January 12, 1993
INVENTOR(S) : Sara J. Risch, et. al.

It is certified that error appears in the above-indentified patent and that said Letters Patent is hereby corrected as shown below:

Column 13, lines 18 and 19, delete "spectrometry system" and insert therefo -- spectograph --.

Signed and Sealed this

Seventh Day of May, 1996

Attest:

BRUCE LEHMAN

Attesting Officer

*Commissioner of Patents and Trademarks*